(12) United States Patent
Zalevsky et al.

(10) Patent No.: US 10,856,739 B2
(45) Date of Patent: Dec. 8, 2020

(54) SYSTEM AND METHOD FOR MONITORING OF OBJECTS WITH INCREASED SENSITIVITY

(71) Applicant: CONTINUSE BIOMETRICS LTD., Tel Aviv (IL)

(72) Inventors: Zeev Zalevsky, Rosh HaAyin (IL); Nisim Nisan Ozana, Rehovot (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 0 days.

(21) Appl. No.: 16/461,856

(22) PCT Filed: Nov. 21, 2017

(86) PCT No.: PCT/IL2017/051269
§ 371 (c)(1),
(2) Date: May 17, 2019

(87) PCT Pub. No.: WO2018/092146
PCT Pub. Date: May 24, 2018

(65) Prior Publication Data
US 2019/0365234 A1 Dec. 5, 2019

Related U.S. Application Data

(60) Provisional application No. 62/424,869, filed on Nov. 21, 2016.

(51) Int. Cl.
*G01B 11/02* (2006.01)
*A61B 5/00* (2006.01)
(Continued)

(52) U.S. Cl.
CPC .......... *A61B 5/0066* (2013.01); *A61B 3/0008* (2013.01); *A61B 5/0051* (2013.01);
(Continued)

(58) Field of Classification Search
CPC ... A61B 5/0066; A61B 5/0051; A61B 5/0048; A61B 3/0008; G01B 9/02094; G01B 9/02095; G01B 11/162
See application file for complete search history.

(56) References Cited

U.S. PATENT DOCUMENTS

| 8,638,991 B2 | 1/2014 | Zalevsky et al. |
| 9,639,041 B2 | 5/2017 | Zalevsky et al. |

(Continued)

FOREIGN PATENT DOCUMENTS

GB  2428093 A  1/2017

OTHER PUBLICATIONS

Ozana et al, "Non-contact speckle based optical sensor for detection of glucose concentration using magneto-optic effect", Journal of Biomedical Optics 21(6), 065001 (2016).

*Primary Examiner* — Tarifur R Chowdhury
*Assistant Examiner* — Jonathon Cook
(74) *Attorney, Agent, or Firm* — Browdy and Neimark, PLLC

(57) ABSTRACT

A system for monitoring parameters of an object is described. The system comprising: a monitoring unit configured for performing one or more monitoring sessions on an object and collecting data from an inspection region on the object over time and generating monitored data indicative of the inspected region, a stimulation unit configured and operable for applying at least one selected external stimulation field on the object during said one or more monitoring sessions, and a control unit configured for receiving the monitored data from the monitoring unit and determining one or more selected parameters. The stimulation unit is configured for providing said at least one selected external stimulation field directed toward said inspection region from two or more different directions. The control unit being configured for utilizing said monitored data in (Continued)

accordance with data on the two or more different directions of the stimulation field applied to the inspection region for determining one or more selected parameters of the object.

10 Claims, 3 Drawing Sheets

(51) Int. Cl.
*A61B 3/00* (2006.01)
*A61B 5/026* (2006.01)
*A61B 5/145* (2006.01)
*G01H 9/00* (2006.01)

(52) U.S. Cl.
CPC .......... *A61B 5/0084* (2013.01); *A61B 5/0261* (2013.01); *A61B 5/14532* (2013.01); *G01H 9/002* (2013.01)

(56) References Cited

U.S. PATENT DOCUMENTS

| | | | |
|---|---|---|---|
| 2008/0055583 A1* | 3/2008 | Lecomte | G01B 11/162 356/32 |
| 2012/0172686 A1 | 7/2012 | Esenaliev et al. | |
| 2014/0148658 A1 | 5/2014 | Zalevsky et al. | |
| 2015/0338208 A1* | 11/2015 | DeWeert | G01B 11/162 356/520 |
| 2016/0025683 A1* | 1/2016 | Davis | G01B 9/02 356/502 |

\* cited by examiner

SYSTEM AND METHOD FOR MONITORING OF OBJECTS WITH INCREASED SENSITIVITY

TECHNOLOGICAL FIELD

The invention is in the field of optical monitoring of an object and relates to monitoring of object's parameters with increased sensitivity with respect to background noise.

BACKGROUND

Optical monitoring using variations in patterns of secondary speckles provide data on mechanical and bio-mechanical parameters of objects and/or biological tissues. These techniques enable detection of nanometric vibrations for determining large variety of bio parameters.

Generally, speckle-based monitoring techniques utilize defocused collection of light reflected or scattered from an inspection region over time to provide a sequence of image data pieces in response to coherent illumination of the inspection region. The so-collected images include secondary speckle patterns formed by self-interference of light components reflected or scattered from the inspection region. The speckle patterns shift in response to changes in the surface of the inspection region, and correlation between speckle patterns in consecutive image data pieces provide data indicative of vibrations of the inspection region.

Monitoring of some mechanical and bio-mechanical parameters can be significantly enhanced using external stimulation applied to the inspected region. Such external stimulation induces reaction on elements in the inspected region that increases desired parameters. Further, the collected speckle patterns may be processed and analyzed at a temporal frequency associated with that of the applied stimulation for extracting selected parameters of the object.

U.S. Pat. No. 8,638,991 describes a method for imaging an object. The method comprises imaging a coherent speckle pattern propagating from an object, using an imaging system being focused on a plane displaced from the object.

U.S. Pat. No. 9,636,041 describes a system and method for monitoring conditions of a subject's body including a control unit receiving image data and data indicative of an external stimulation applied to the body during collection of the image data therefrom, a memory utility, and a processor utility. The image data is indicative of a sequence of speckle patterns generated by the body according to a certain sampling time pattern. The processor utility performs processing the image data utilizing the data indicative of the applied external field(s), including determining a spatial correlation function between successive speckle patterns in the sequence, and determining a time varying spatial correlation function in the form of a time-varying function of a feature of the correlation function indicative of a change of the speckle pattern over time; selecting a parameter of the time-varying spatial correlation function, and applying a model to the parameter to determine a corresponding body condition; and generating output data indicative of the corresponding body condition.

GENERAL DESCRIPTION

There is a need in the art for a novel technique enabling monitoring of parameters of an object with increased sensitivity, i.e. increased signal to noise ratio. Generally, effects of noise may reduce sensitivity of measurements limiting the ability of detecting small variations and weak signals. The present invention provides a system and method for monitoring one or more selected parameters of an object or a biological tissue, while reducing the effects of noise in the detected signals, by using dependence of the measured signal on directionality of external stimulation being applied on the object being measured.

The speckle-based sensing technology, as described in the above-indicated U.S. Pat. Nos. 8,638,991 and 9,636,041, provides detection of nanometric vibrations and may be used for bio-medical sensing of large variety of bio parameters. The sensitivity and the selectivity of the signal detection can be enhanced by using an external stimulus for detection of certain parameters. Usage of the stimulus can significantly enhance the signal to noise ratio (SNR) of the measurement as the speckle patterns may be analyzed at the temporal frequency of the stimulation and from there the signal can be extracted.

The noise, on the other hand, typically includes white noise containing wide range of temporal spectral frequencies, and thus the SNR can be increased by performing measurement with sampling at known frequency associated with that of the desired signals.

The technique of the present invention provides a further increase of the SNR using data about directionality of an external stimulation applied to object during measurements, or using such directionality data of the external stimulating field in addition to a selected sampling frequency as described herein below.

To this end, the present technique provides for monitoring parameters of an object utilizing a selected external excitation applied on the object during measurements. A measurement system of the invention comprises: a monitoring unit configured for collecting data indicative of an inspection region on the object, a stimulation unit configured for providing an external stimulation of a selected profile on the object, and a control unit configured for receiving monitored data from the monitoring unit and determining one or more selected parameters. Generally, the stimulation field applied on, or in vicinity of, the inspection region is used for enabling extraction of one or more selected properties of the sample by monitoring thereof using the monitoring unit. The stimulation unit is configured for selectively applying the stimulation field from two or more directions toward the inspection region. To this end, the stimulation unit may include one or more stimulators configured to be moveable or rotatable with respect to orientation of the object (or with respect to the monitoring unit, for a given orientation between the monitoring unit and the object) or to be stationary positioned and electronically operable to vary the direction of propagation of the stimulation field being generated by said one or more stimulators, thereby enabling monitoring of the object's response to excitation fields arriving from different directions. Alternatively, or additionally, the stimulation unit may include two or more stimulators mounted at selected different positions with respect to the inspection region and configured to be selectively operated such that the provided stimulation fields propagate through selected different directions toward the inspection region. For example, the stimulation unit may be mounted on a moving frame, selectively operable for varying direction of external stimulation/excitation field applied to the inspection region during monitoring period. On another example, the stimulation unit may include two or more stimulators mounted on different locations of a frame and sequentially operable, thereby varying direction of stimulation field.

The control unit is typically configured as a computing system, including, e.g., one or more processors, storage utility and input/output (I/O) communication connections, and is configured for utilizing monitored data collected by the monitoring unit in accordance with data on the varying direction of the stimulation applied to the inspection region for determining said one or more selected parameters.

The control unit is generally configured for processing the collected monitored data in accordance with data indicative of variations in direction of the external stimulation applied on the object during the collection of the monitored data, in order to average out noise in the collected data, thus increasing signal to noise ratio. This is based on the inventors' understanding that while the external stimulation field has certain directionality, and variation of the direction of the stimulation field affects the inspection region (monitored parameters thereof) accordingly, the background noise is generally isotropic and is not affected by variations of directionality of the stimulation field. For example, input monitored data collected with one direction of stimulation field may be compared to data collected with a different direction of stimulation, e.g. by determining difference between the measurements, to average out noise levels and determine data about desired parameter to be measured.

Thus, according to a broad aspect, the present invention provides a system for monitoring parameters of an object, the system comprising: a monitoring unit configured for performing one or more monitoring sessions on an object and collecting data from an inspection region on the object over time and generating monitored data indicative of the inspected region, a stimulation unit configured and operable for applying at least one selected external stimulation field on the object during said one or more monitoring sessions, and a control unit configured for receiving the monitored data from the monitoring unit and determining one or more selected parameters;

wherein said stimulation unit is configured for providing said at least one selected external stimulation field directed toward said inspection region from two or more different directions, said control unit being configured for utilizing said monitored data in accordance with data on the two or more different directions of the stimulation field applied to the inspection region for determining one or more selected parameters of the object.

According to some embodiments, the monitoring unit may comprise an optical collection unit comprising an optical imaging arrangement and a detector array, said optical collection unit is configured for collecting defocused image data pieces associated with light returning from the inspection region in response to coherent illumination thereof, said image data pieces comprise secondary speckle patterns formed by self-interference of light components returning from the inspection region.

The monitoring unit may further comprise a light source unit configured for providing coherent optical illumination and for directing said optical illumination onto the inspection region.

The stimulation unit may be configured for applying magnetic field excitation, acoustic excitation, or other stimulation fields toward the inspection region.

According to some embodiments, the stimulation unit may comprise at least one stimulator mounted on a moving frame, said moving frame being selectively operable for varying location of said at least one stimulator, thereby varying direction of external stimulation applied to the inspection region during monitoring period.

According to some embodiments, the stimulation unit comprises two or more stimulators mounted at corresponding two or more selected positions for providing stimulation fields propagating through corresponding different directions toward said inspection region, said control unit being configured for selectively operating said two or more stimulators for selectively varying direction of stimulation for one or more during monitoring periods.

Generally, the control unit may be configured for operating the monitoring unit and stimulation unit for collecting two or more sequences of monitored data, and for processing the two or more sequences and determining signal variation between the sequences collected with different direction of the stimulation unit.

According to one other broad aspect, the present invention provides a method for use in monitoring of an object, the method comprising:

applying selected stimulation field from a first direction toward an inspection region on the object, and monitoring response of the inspection region for a selected collection period;

varying direction of the stimulation field to another direction and monitoring response of the inspection region for the selected collection period;

providing collected data sequences associated with two or more directions of stimulation and processing the sequences of collected data for determining variation in signals associated with variations of stimulation direction;

generating data indicative of response of the inspection region in accordance with signal changes between different stimulation directions.

According to some embodiments, said varying direction of the stimulation field comprises selectively switching one or more stimulators for providing stimulation field arriving from one direction and operating one or more other stimulators for providing stimulation field arriving from one other direction.

According to some other embodiments, said varying direction of the stimulation field comprises selectively moving one or more stimulators from one selected position to one other selected position for directing stimulation field from another direction.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
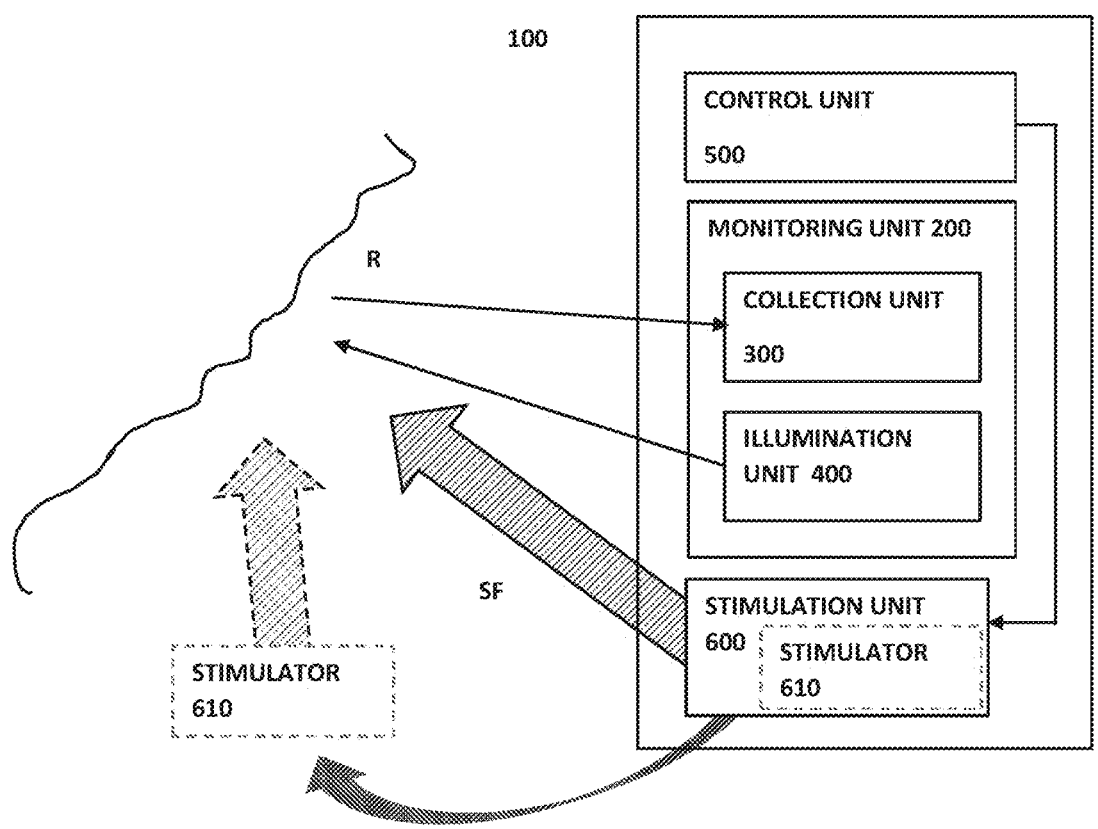
FIG. 1 illustrates a system for monitoring an object according to some embodiments of the invention.

As indicated above, the present technique provides for monitoring parameters of an objects with enhances sensitivity and increased signal to noise ratio (SNR). Reference is made to FIG. 1 illustrating schematically a system 100 for monitoring of an object as described herein. The system includes a monitoring unit 200 and stimulation unit 600 and configured for monitoring parameters of an objects, or an inspection region R thereof, while applying selected stimulation field SF on the region R. The stimulation unit 600 is configured for selectively providing stimulation field from two or more directions toward the inspection region R. To this end, the stimulation unit may include one or more stimulators 610 mounted on a moveable or rotatable arm (the arm is not specifically shown in the figure), or include two or more stimulators 610 positioned at corresponding different locations and selectively operable. This configuration of the stimulation unit 600 enables the system 100 to vary direction of the stimulation field SF and accordingly to monitor variations in response of the inspection region to stimulation arriving from different directions. This may be used for distinguishing signal data, which may generally be associated with the stimulation field and therefore vary with direction of the stimulation, from background noise that is typically not directional. System 100 typically also includes a control unit 500 configured for operating the monitoring 200 and stimulation 600 units, and the rotatable arm when used, and for receiving input data from the monitoring unit for processing. According to the present technique, the data (monitored data) is collected from the inspection region, with respect to stimulation field SF applied thereon from two or more directions. Processing of the monitored data for determining one or more selected parameters of the object, is based on the inventors' understanding that features of the collected data associated with the object's response to the stimulation field vary in accordance with direction of the stimulation field. This is while noise appearing in the monitored data and reducing sensitivity and accuracy, is generally white noise that is not affected by variation of direction of the stimulation field.

According to some embodiments, the monitoring unit 200 may be configured as optical monitoring unit. In some configurations, the optical monitoring unit may be configured for spackle based monitoring of the inspection region R. To this end, the monitoring unit may include at least an illumination unit 400 and a collection unit 300. The illumination unit 400 is configured for providing coherent illumination directed onto the inspection region R. The collection unit 300 includes a detector array and optical arrangement configured for collecting defocused image data of the region of interest R and directing it to the detector array. This configuration of the collection unit, provides for collection of image data pieces associated with patterns of secondary speckles generated by self-interference of light components after reflection and scattering from the inspection region R. Correlations between the consecutively collected speckle patterns provide data indicative of variations in location, orientation and curvature of the inspection region R and may accordingly provide data on various parameters of the inspected region. Generally, in this configuration, the collection unit 300 is operable for collecting a sequence of image data pieces at a selected frame rate, and the control unit is operable for processing the collected image data pieces, determining at least one correlation function along the sequence of image data pieces, and utilizing the correlation function for determining one or more parameters of the inspection region R.

As indicated above, for determining certain parameters of biological tissues, the above-mentioned speckle-based monitoring generally utilizes external stimulation applied on, or in vicinity of, the inspection region R. To this end, the stimulation unit 600 includes one or more stimulators 610 configured for providing selected stimulation field and for directing it toward the inspection region R. The stimulation field may for example include electromagnetic field stimulation, e.g. static or alternating magnetic field, acoustic stimulation, mechanical vibration etc. The external stimulation field enables detection of selected features by interacting with the object at the inspection region in a way that can be detected using the monitoring unit 200. For example, glucose concertation in the blood stream can be detected using detection of Faraday rotation effect generated by interaction of light with the glucose molecules in presence of magnetic fields. This is described in more details by Ozana et al, *"Non-contact speckle based optical sensor for detection of glucose concentration using magneto-optic effect"*, Journal of Biomedical Optics 21(6), 065001 (2016). The use of external stimulation generates and/or increases signals associated with specific parameters for monitoring. However, it is typically desired to further increase the signal over background noise and optimize sensitivity of monitoring. One technique for increasing the SNR is associated with tuning the sampling rate with frequency of the stimulation field. This technique provides for lock-in amplification for signals of the same frequency while reducing noise effects that appear in all frequencies (white noise).

Further, the inventors of the present invention have found that the measurements can be significantly improved by additional increase in the signal to noise ratio which may be achieved using geometrical and topological relations between the sought signal and external stimulations applied on the inspection region. More specifically, as the external stimulation field applied on the inspection region has certain directionality, variation of the direction of the stimulation field may affect the signal while the background noise is generally not affected.

Accordingly, the present technique utilizes the property of directionality to enhance and to further improve the SNR. In the example of the Faraday rotation effect, the effect, and accordingly the measured signals, is dependent on the direction of the magnetic field (the optical wavefront is dependent on the direction of the magnetic field and the changes in the optical wavefront change the sensed speckle patterns). Thus, if the magnetic field is applied at a given temporal frequency but its direction is also changed in time in a controlled manner, the collected signal (e.g. speckle patterns) will also change in time. On the other hand, the noise, e.g. vibration related noise, is not affected by a change in direction of the stimulation. This is true even if the noise is associated with the stimulation, e.g. depending on stimulation frequency.

Accordingly, in some configurations, the system 100 as described herein is provided with a stimulation unit 600, including a stimulator 610 mounted on a rotatable or moveable arm configured for selectively varying location and/or orientation of the stimulation field applied on the inspection region R. More specifically, in some configurations, the stimulator 610 may be mounted on a moveable/rotatable arm enabling to rotate the stimulator 610 about a selected axis to vary the direction of stimulation field with respect to the inspection region. In this connection, the stimulator may be configured as magnetic coil or acoustic transducer thereof, where the stimulation unit 600 includes the required control, wiring, power source etc. Further, in some configurations, the stimulation unit 600 by itself is mounted to be rotatable or moveable as a complete unit.

In some other configurations, the stimulation unit 600 may include two or more stimulators 610 mounted in selected positions and are selectively operable for varying direction of the stimulation field. More specifically, a first stimulator 610 may be operated in a first monitoring period, second stimulator operated in a second monitoring period etc. In some additional configurations, two or more stimulators may be operated simultaneously with selected operation intensity (field intensity) thereby resulting in effective stimulation fields of selected directions.

Figure 2:
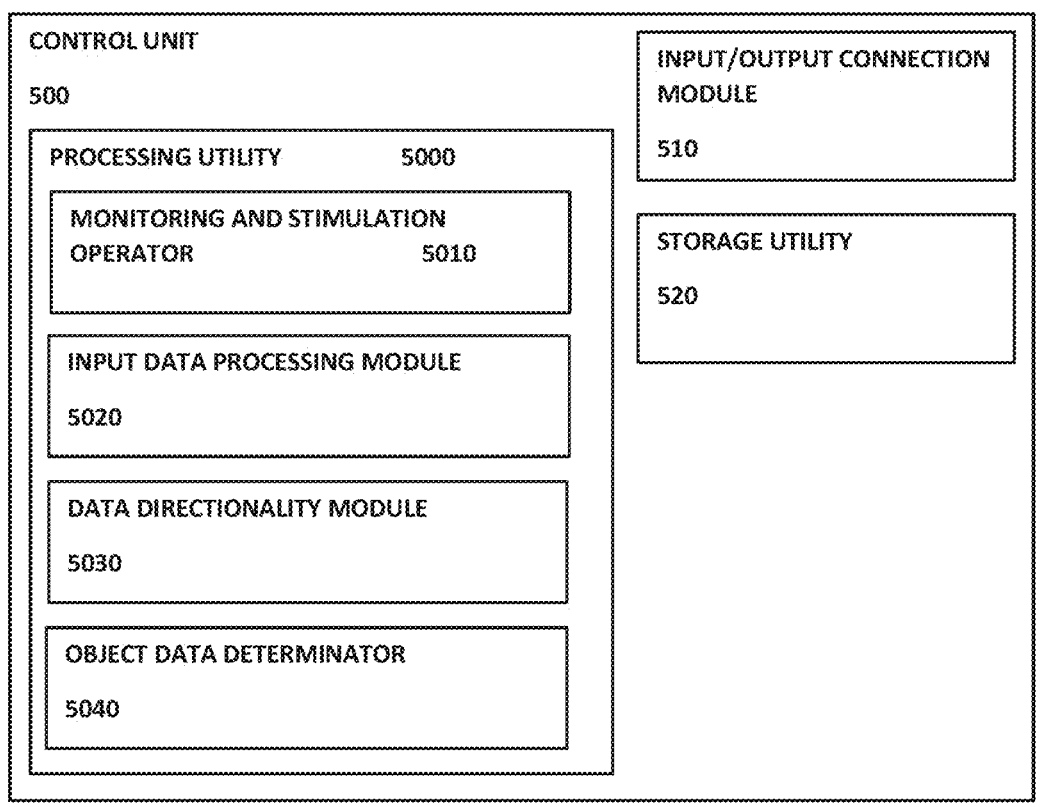
FIG. 2 illustrates configuration of a control unit for use in system for monitoring an object according to some embodiments of the invention.

The control unit 500 is configured for operating the monitoring unit 200 and the stimulation unit 600 and for processing the monitored data in accordance with the present technique. Reference is made to FIG. 2 illustrating a configuration of the control unit 500 according to some embodiments of the invention. As indicated above, the control unit may be configured as a computer system including one or more processors, defined herein as processing utility 5000, storage utility 520 and input/output communication ports 510, e.g. including user interface, network communication path and wired or wireless communication lines with the monitoring and stimulation units 200 and 600. Generally, the control unit is configured for operating in accordance with pre-stored computer readable instructions, e.g. stored in the storage utility, and may receive selected parameters from an operator (human or software). To this end, the processing utility 5000 may include one or more software or hardware modules for corresponding tasks.

As shown, the processing utility includes monitoring and stimulation operator 5010 configured for generating and transmitting operational commands to the monitoring unit 200, stimulation unit 600, as well as a drive mechanism of the moveable arm when configured for receiving separated commands; input data processing module 5020 configured for receiving input data indicative of data collected by the monitoring unit 200 and provide selected pre-processing; data directionality module 5030 configured for processing two or more sets of pre-processed input data streams in accordance with data about variations in directionality of the stimulation field, to determine effects of direction changes on the collected data; and object data determinator module 5040 configured for processing the sets of collected data in accordance with effects of changes in direction of stimulation field for determining data on one or more selected properties of the inspection region.

Generally, the control unit 500, e.g. using the monitoring and stimulation operator 5010, may be configured for operating the stimulation unit 600 for providing stimulation field of selected parameters (e.g. amplitude and frequency) from first direction and at the same time operating the monitoring unit 200 for obtaining monitoring data for a selected time period. After collecting data about the object's response to stimulation in one direction, the control unit may operate the moveable arm for varying position thereof to enable stimulation of the inspection region from a different direction, and operate the monitoring unit 200 for obtaining data. The control unit may operate the stimulation 600 and monitoring 200 units for performing two or more monitoring sessions and obtaining respective two or more sequences of monitored data associated with stimulation from two or more different directions. These data are received by the control unit for processing and/or storing for later use or transmitting to remote processing.

The input data processing module 5020 is configured for receiving input data associated with each monitoring sequence and, when needed, apply selected pre-processing thereon. For example, in the non-limiting configuration of speckle-based monitoring, each monitoring sequence data includes a sequence of image data pieces including speckle patterns generated by self-interference of light components reflected and scattered from the inspection region. In this configuration, the input data processing module 5020 may be configured and operable for determining one or more correlation functions between the consecutive image data pieces. The one or more correlation function is generally indicative of vibrations at the inspection region, in response to the stimulation field applied thereto.

The input data processing module 5020 may also be configured for providing one or more noise reduction processing or other filtering of the input data. In some other configurations, e.g. utilizing direct monitoring of the inspection region, the input data processing module 5020 may be associated with input of transmitted data and transmitting the data for processing, or be omitted.

The data directionality module 5030 is configured for receiving data on two or more monitoring sequences, and for processing the input monitoring sequences for determining variation of collected signal between the sequences. The variation in the collected signal may typically be associated with variation of signal directions or distribution of directions, such as directions of movement/vibrations of the inspection region in any one of possible six degrees of movement or relations between vibration amplitude along different axes, spatial distribution, general amplitude of the signal, changes in light polarization etc. The data processing technique may determine variations in raw collected signals with respect to changes in direction of stimulation field. However, in some preferred embodiments, the technique, using the control unit, may operate for processing collected monitoring data and determining data associated with interaction of the inspected region with the stimulation field for each direction of the stimulation filed. This enables identifying variation in the determined/monitored response of the inspected region over variations in the collected data as is.

For example, in the case of speckle-based monitoring, the data directionality module 5030 may receive data on one or more correlation functions determined between image data pieces of the monitoring sequences. The correlation functions are generally indicative of vibrations of the inspection region in response to the stimulation applied thereon. Accordingly, variation of the stimulation direction may vary direction of the response, while not changing direction of the background noise vibrations. In this connection, the data directionality module 5030 may operate for processing the correlation functions and determining data on vibrations of the inspection region in three or more dimensions, i.e. vibrations along three axes (x, y and z) and/or changes in curvature in three axes. The data directionality module 5030 is typically configured for determining one time dependent response function indicative of the differences in response of the inspection region to stimulations applied from two or more different directions, providing data indicative of response of the inspected tissue with reduction of background noise. The data directionality module 5030 generally transmits data on the time dependent response function to the object data determinator module 5040 and/or for storage and/or remote processing in accordance with specific configuration of the system.

The object data determinator 5040 is configured for receiving data on the time dependent response function, and for processing and analyzing the time dependent response function in accordance with pre-provided data on the inspection region R, stimulation type and desired properties of the object, to thereby generate output data indicative of the object properties. To this end the object data determinator 5040 may utilize pre-provided lookup table stored in the storage utility 520 or in remote storage (via network communication) for comparing response of the inspection region with relevant properties of the inspection region. For example, the selected object properties may be associated with glucose concentration, determined in accordance with detection of Faraday Effect in response to AC magnetic field applied on a subject's hand (or other inspection region). Alternatively, the selected property may be associated with intra-cranial-pressure (ICP) determined external examining the vibration responsivity of the eardrum with response to ultra-sonic stimulation. Generally, the endolymph liquid accumulated in the inner part of the eardrum may be associated to the ICP and its accumulation in proximity to the eardrum may affect the vibrational responsivity of the eardrum to stimulations of external pressure waves. The present technique may also be used for determining data on peripheral artery diseases, where the stiffness of the inspected artery is detected by monitoring response to stimulation by pressure waves as compared to reference representing healthy condition. Additional properties may be associated with bone density measured in response to acoustic or ultra-sonic stimulation in elastography measurements; or density of other tissue types for determining data on tumors. Other such applications may be associated with general elastography measurements including biological or non-biological samples, as the case may be.

Figure 3:
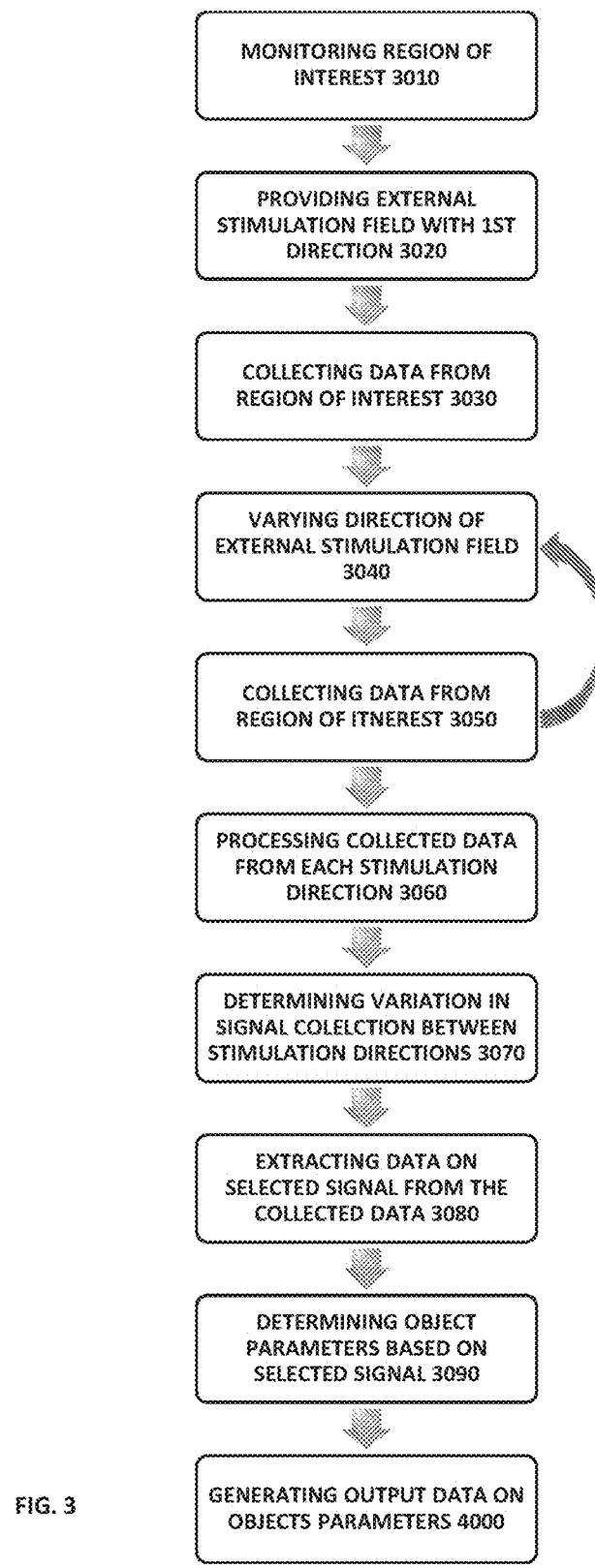
FIG. 3 shows a block diagram flow a method for monitoring an object according to some embodiments of the invention.

The technique as described above is schematically illustrated in FIG. 3. As shown, the technique including monitoring of a selected region of interest 3010, while at the same time applying selected stimulation field directed from a first direction 3020 on to, on to vicinity of, the region of interest. The response of the inspection region is collected 3030 to provide first monitoring sequence data. It should be noted that the desired monitored data is collected during operation of the stimulation field.

After collecting one monitoring sequence, the technique includes varying direction from which the stimulation field is applied toward the inspection region 3040. The technique may utilize moveable or rotatable arm configured for mounting a stimulation unit as described above, and vary location/orientation of the arm. After providing a new direction for the stimulation field, additional sequence of monitoring data is collected 3050, including monitoring data on the response of the inspection region to stimulation from the current direction. Generally, the technique includes collecting data associated with two or more directions of stimulation. This may include three directions, four directions, five directions etc.

The sets/sequences of collected data are transmitted for processing 3060. Generally, in some embodiments, the technique may apply selected pro-processing onto each set of collected data separately (e.g. determining one or more correlations functions between speckle patterns in collected data) for preparing the collected data. Further, the technique includes processing of the different sets together for determining signal variations between sequences associated with stimulation of different directions 3070. As indicated above, the signal may typically vary in accordance with direction of the applied stimulation, while the background noise typically does not response to direction of the stimulation. This provides greater signal to noise ratio and enables increased sensitivity and accuracy of monitoring.

In accordance with variations between signals collected in different sets, the technique includes extracting response function data on the signal 3080, typically selected in accordance with desired property for inspection. The technique further utilizes determining 3090, in accordance with the response function data, one or more object parameters. This is based on processing the collected signal, e.g. in accordance with one or more lookup tables or database, in accordance with the response of the inspection region to stimulation, and generating corresponding output data 4000 to user/operator or transmitting the output data for further processing.

Thus, the present invention provides a novel technique where the directionality of the external stimulation is used in order to enhance the SNR of monitored data. This may be applied in speckle based sensing, as well as in additional sensing techniques. The directionality SNR enhancement is generally used with external stimulation such as magnetic field excitation or acoustic stimulation (ultra-sonic sonic or infra-sonic) or other pressure wave stimulations. For speckle based sensing techniques, the present technique may be used for enhanced detection of glucose concentration ICP, peripheral artery diseases, as well as structural health monitoring of pipes, buildings and constructs.

The invention claimed is:

1. A system for monitoring parameters of an object, the system comprising:
a monitoring unit comprising an optical collection unit configured for performing two or more monitoring sessions on an object, each monitoring session comprising collecting data from an inspection region on the object over time and generating monitored data comprising a sequence of image data pieces indicative of the inspected region during said monitoring session, the optical collection unit comprising an optical imaging arrangement and a detector array configured for collecting defocused image data pieces comprising secondary speckle patterns formed by self-interference of light components returning from the inspection region;
a stimulation unit configured and operable for applying at least one selected external stimulation field on the object during said one or more monitoring sessions, and
a control unit configured for receiving and processing the monitored data from the monitoring unit for said two or more monitoring sessions and determining one or more selected parameters;
wherein said stimulation unit is configured for providing said at least one selected external stimulation field directed toward said inspection region from two or more different directions for said two or more monitoring sessions respectively, and
wherein said control unit is configured for processing said monitored data from said two or more monitoring sessions associated with external stimulation field applied to the inspection region from two or more different directions and for determining object data based on variations in the one or more selected parameters of the object determined from data collected in said two or more monitoring sessions.

2. The system of claim 1, wherein said monitoring unit further comprises a light source unit configured for providing coherent optical illumination and for directing said optical illumination onto the inspection region.

3. The system of claim 1, wherein said stimulation unit is configured for applying magnetic field excitation toward the inspection region.

4. The system of claim 1, wherein said stimulation unit is configured for applying acoustic excitation toward the inspection region.

5. The system of claim 1, wherein said stimulation unit comprises at least one stimulator mounted on a moving frame, said moving frame being selectively operable for varying location of said at least one stimulator with respect to said monitoring unit and said object, thereby varying direction of external stimulation applied to the inspection region during monitoring period.

6. The system of claim 1, wherein said stimulation unit comprises two or more stimulators mounted at corresponding two or more selected positions for providing stimulation fields propagating through corresponding different directions toward said inspection region, said control unit being configured for selectively operating said two or more stimulators for selectively varying direction of stimulation for one or more during monitoring periods.

7. The system of claim 1, wherein said control unit is configured for operating the monitoring unit and stimulation unit for collecting two or more sequences of monitored data, and for processing the two or more sequences and determining signal variation between the sequences collected with different direction of the stimulation unit.

8. A method for use in monitoring of an object, the method comprising:
applying selected stimulation field from a first direction toward an inspection region on the object, and monitoring response of the inspection region for a selected collection period, said monitoring comprises providing coherent illumination impinging on at least said inspection region on the object and collecting a sequence of image data pieces being defocused with respect to said inspection region and being indicative of secondary speckle patterns returning from the object;
varying direction of the stimulation field to another direction and monitoring response of the inspection region for the selected collection period by collecting an additional sequence of image data pieces being defocused with respect to the inspection region, and being indicative of secondary speckle patterns returning from the object in response to coherent illumination;
providing collected data sequences associated with two or more directions of stimulation and processing the sequences of collected data by determining time varying spatial correlation function indicative of correlations between the defocused image data pieces;
determining variation in time varying spatial correlation function between said data sequences associated with said two or more directions of stimulation;
generating data indicative of response of the inspection region in accordance with signal changes between different stimulation directions.

9. The method of claim 8, wherein said varying direction of the stimulation field comprises selectively switching one or more stimulators for providing stimulation field arriving from one direction and operating one or more other stimulators for providing stimulation field arriving from one other direction.

10. The method of claim 8, wherein said varying direction of the stimulation field comprises selectively moving one or more stimulators from one selected position to one other selected position for directing stimulation field from another direction.

* * * * *